United States Patent
Romo et al.

(10) Patent No.: US 10,653,546 B2
(45) Date of Patent: May 19, 2020

(54) ORTHOPEDIC DEVICE HAVING A DYNAMIC CONTROL SYSTEM

(71) Applicant: OSSUR HF, Reykjavik (IS)

(72) Inventors: Harry Duane Romo, Aliso Viejo, CA (US); Christopher Callicott Webster, Irvine, CA (US); Jared Olivo, Highland, CA (US)

(73) Assignee: OSSUR HF, Reykjavik (IS)

( * ) Notice: Subject to any disclaimer, the term of this patent is extended or adjusted under 35 U.S.C. 154(b) by 780 days.

(21) Appl. No.: 14/926,098

(22) Filed: Oct. 29, 2015

(65) Prior Publication Data

US 2016/0120683 A1 May 5, 2016

Related U.S. Application Data

(60) Provisional application No. 62/073,797, filed on Oct. 31, 2014.

(51) Int. Cl.
*A61F 5/01* (2006.01)

(52) U.S. Cl.
CPC .... *A61F 5/0123* (2013.01); *A61F 2005/0134* (2013.01); *A61F 2005/0144* (2013.01); *A61F 2005/0165* (2013.01); *A61F 2005/0179* (2013.01)

(58) Field of Classification Search
CPC ............ A61F 2005/0134; A61F 5/0123; A61F 5/0125; A61F 5/01; A61F 5/0102
USPC ........................ 602/16, 5, 12, 23, 26; 601/33
See application file for complete search history.

(56) References Cited

U.S. PATENT DOCUMENTS

| | | | |
|---|---|---|---|
| 73,768 | A | 1/1868 | Allen |
| 1,601,659 | A | 9/1926 | Van Harlingen |
| 2,195,024 | A | 3/1940 | Bullock |
| 2,467,907 | A | 4/1949 | Peckham |
| 2,536,454 | A | 1/1951 | Mcintyre |

(Continued)

FOREIGN PATENT DOCUMENTS

| | | |
|---|---|---|
| DE | 33 20 274 A1 | 12/1984 |
| DE | 196 31 632 A1 | 2/1998 |

(Continued)

OTHER PUBLICATIONS

Defrate, Louis E., et al., "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.

(Continued)

*Primary Examiner* — Anna K Kinsaul
*Assistant Examiner* — Caitlin A Carreiro
(74) *Attorney, Agent, or Firm* — Workman Nydegger

(57) ABSTRACT

An orthopedic device has first and second struts connected to one another by a hinge system, and includes a dynamic control system and a counterforce system. The dynamic control system includes first and second dynamic components arranged on a first side of the orthopedic device to exert first and second dynamic forces according to a flexion angle of the hinge system. A counterforce system is located on a second side of the orthopedic device to counteract the first and second dynamic forces with at least one counterforce.

16 Claims, 5 Drawing Sheets

(56) References Cited

U.S. PATENT DOCUMENTS

| | | |
|---|---|---|
| 2,558,986 A | 7/1951 | Seelert |
| 2,959,168 A | 11/1960 | Shook |
| 3,316,900 A | 5/1967 | Young |
| 3,348,812 A | 10/1967 | Story |
| 3,444,560 A | 5/1969 | Northup, Jr. |
| 3,753,625 A | 8/1973 | Fabrizio et al. |
| 3,947,156 A | 3/1976 | Becker |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,298,992 A | 11/1981 | Burnstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,397,308 A | 8/1983 | Hepburn |
| 4,407,276 A | 10/1983 | Bledsoe |
| 4,428,369 A | 1/1984 | Peckham et al. |
| 4,433,679 A | 2/1984 | Mauldin et al. |
| 4,463,751 A | 8/1984 | Bledsoe |
| 4,489,718 A | 12/1984 | Martin |
| 4,506,661 A | 3/1985 | Foster |
| 4,508,111 A | 4/1985 | Hepburn |
| 4,520,802 A | 6/1985 | Mercer et al. |
| 4,523,585 A | 6/1985 | Lamb et al. |
| 4,649,906 A | 3/1987 | Spademan |
| 4,655,201 A | 4/1987 | Pirmantgen |
| 4,657,000 A | 4/1987 | Hepburn |
| 4,691,694 A | 9/1987 | Boyd et al. |
| 4,697,583 A | 10/1987 | Mason et al. |
| 4,723,539 A | 2/1988 | Townsend |
| 4,732,143 A | 3/1988 | Kausek et al. |
| 4,733,656 A | 3/1988 | Marquette |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,817,588 A | 4/1989 | Bledsoe |
| 4,856,500 A | 8/1989 | Spademan |
| 4,856,501 A | 8/1989 | Castillo et al. |
| 4,865,024 A | 9/1989 | Hensley et al. |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,966,133 A | 10/1990 | Kausek |
| 4,982,732 A | 1/1991 | Morris |
| 4,991,571 A | 2/1991 | Kausek |
| 5,002,045 A | 3/1991 | Spademan |
| 5,018,514 A | 5/1991 | Grood et al. |
| 5,020,797 A | 6/1991 | Burns |
| 5,038,765 A | 8/1991 | Young et al. |
| 5,052,375 A | 10/1991 | Stark et al. |
| 5,063,917 A | 11/1991 | Young et al. |
| 5,176,622 A | 1/1993 | Anderson et al. |
| 5,213,094 A | 5/1993 | Bonutti |
| 5,230,696 A | 7/1993 | Silver et al. |
| 5,230,697 A | 7/1993 | Castillo et al. |
| 5,261,871 A | 11/1993 | Greenfield |
| 5,347,894 A | 9/1994 | Fischer |
| 5,357,654 A | 10/1994 | Hsing-Chi |
| 5,437,611 A | 8/1995 | Stern |
| 5,443,444 A | 8/1995 | Pruyssers |
| 5,456,268 A | 10/1995 | Bonutti |
| 5,472,410 A | 12/1995 | Hamersly |
| 5,472,412 A | 12/1995 | Knoth |
| 5,514,082 A | 5/1996 | Smith, III |
| 5,575,764 A | 11/1996 | Van Dyne |
| 5,588,956 A | 12/1996 | Billotti |
| 5,599,288 A | 2/1997 | Shirley et al. |
| 5,624,390 A | 4/1997 | Van Dyne |
| 5,628,722 A | 5/1997 | Solomonow et al. |
| 5,658,241 A | 8/1997 | Deharde et al. |
| 5,662,596 A | 9/1997 | Young |
| 5,683,353 A | 11/1997 | Hamersly |
| 5,685,830 A | 11/1997 | Bonutti |
| 5,807,294 A | 9/1998 | Cawley et al. |
| 5,827,208 A | 10/1998 | Mason et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Sterns et al. |
| 5,921,946 A | 7/1999 | Tillinghast et al. |
| 5,934,599 A | 8/1999 | Hammerslag |
| 5,950,245 A | 9/1999 | Binduga |
| 5,954,677 A | 9/1999 | Albrecht et al. |
| 5,997,493 A | 12/1999 | Young |
| 6,001,075 A | 12/1999 | Clemens et al. |
| 6,004,283 A | 12/1999 | Young |
| 6,074,355 A | 6/2000 | Bartlett |
| 6,110,137 A | 8/2000 | Bastyr et al. |
| 6,110,138 A | 8/2000 | Shirley |
| 6,129,690 A | 10/2000 | Hamlin et al. |
| RE37,209 E | 6/2001 | Hensley et al. |
| 6,245,034 B1 | 6/2001 | Bennett et al. |
| RE37,297 E | 7/2001 | Smith, III |
| 6,290,664 B1 | 9/2001 | Nauert |
| 6,331,169 B1 | 12/2001 | Bastyr et al. |
| 6,409,693 B1 | 6/2002 | Brannigan |
| 6,413,232 B1 | 7/2002 | Townsend et al. |
| 6,425,166 B1 | 7/2002 | Seligman et al. |
| 6,436,058 B1 | 8/2002 | Krahner et al. |
| 6,471,664 B1 | 10/2002 | Campbell et al. |
| 6,500,138 B1 | 12/2002 | Irby et al. |
| 6,551,264 B1 | 4/2003 | Cawley et al. |
| 6,666,837 B2 | 12/2003 | Weihermuller |
| 6,740,054 B2 | 5/2004 | Sterns |
| 6,752,775 B2 | 6/2004 | Seligman et al. |
| 6,834,752 B2 | 12/2004 | Irby et al. |
| 6,875,187 B2 | 4/2005 | Castillo |
| 6,936,020 B2 | 8/2005 | Davis |
| 6,993,808 B1 | 2/2006 | Bennett et al. |
| 7,004,919 B2 | 2/2006 | Gaylord et al. |
| 7,037,287 B2 | 5/2006 | Cormier et al. |
| 7,059,329 B2 | 6/2006 | Mason et al. |
| 7,074,201 B2 | 7/2006 | Reinecke et al. |
| 7,097,627 B2 | 8/2006 | Enzerink et al. |
| 7,117,569 B2 | 10/2006 | Bledsoe |
| 7,150,721 B2 | 12/2006 | Houser |
| 7,182,740 B1 | 2/2007 | Castillo |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,207,960 B2 | 4/2007 | Kenney |
| 7,235,058 B2 | 6/2007 | Doty et al. |
| 7,235,059 B2 | 6/2007 | Mason et al. |
| 7,309,322 B2 | 12/2007 | Albrecht et al. |
| 7,311,687 B2 | 12/2007 | Hoffmeier et al. |
| D577,828 S | 9/2008 | Ingimundarson et al. |
| 7,431,708 B2 | 10/2008 | Sreeramagiri |
| 7,435,234 B2 | 10/2008 | Gamada |
| 7,485,103 B2 | 2/2009 | Mason et al. |
| 7,500,957 B2 | 3/2009 | Bledsoe |
| 7,534,217 B2 | 5/2009 | Seligman et al. |
| 7,534,219 B2 | 5/2009 | Sterns |
| 7,544,174 B2 | 6/2009 | Nathanson |
| 7,553,289 B2 | 6/2009 | Cadichon |
| 7,597,675 B2 | 10/2009 | Ingimundarson et al. |
| 7,662,122 B2 | 2/2010 | Sterling |
| 7,722,555 B2 | 5/2010 | Doty et al. |
| 7,727,174 B2 | 6/2010 | Chang et al. |
| 7,749,183 B2 | 7/2010 | Ingimundarson et al. |
| 7,757,303 B2 | 7/2010 | Miller |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |
| 7,927,299 B2 | 4/2011 | Krause |
| 7,963,933 B2 | 6/2011 | Nace |
| 8,048,013 B2 | 11/2011 | Ingimundarson et al. |

(56) References Cited

U.S. PATENT DOCUMENTS

| | | | |
|---|---|---|---|
| 8,128,587 | B2 | 3/2012 | Stevenson et al. |
| 8,376,974 | B2 | 2/2013 | Nace |
| 8,882,688 | B1 | 11/2014 | Ancinec |
| 8,920,350 | B2 | 12/2014 | Merkley et al. |
| 9,220,624 | B2 | 12/2015 | Jansson et al. |
| 9,539,135 | B2 | 1/2017 | Romo et al. |
| 2002/0013544 | A1 | 1/2002 | Sterns |
| 2002/0052568 | A1 | 5/2002 | Houser et al. |
| 2002/0052663 | A1 | 5/2002 | Herr et al. |
| 2002/0133108 | A1 | 9/2002 | Jagodzinski |
| 2004/0002674 | A1 | 1/2004 | Sterling |
| 2004/0030411 | A1 | 2/2004 | Caspers |
| 2004/0049140 | A1 | 3/2004 | Doty et al. |
| 2004/0049290 | A1 | 3/2004 | Bedard |
| 2004/0054307 | A1 | 3/2004 | Mason et al. |
| 2004/0054311 | A1 | 3/2004 | Sterling |
| 2004/0068215 | A1 | 4/2004 | Adelson et al. |
| 2004/0097859 | A1 | 5/2004 | Sterns |
| 2005/0015156 | A1 | 1/2005 | Hikichi |
| 2005/0020951 | A1 | 1/2005 | Gaylord et al. |
| 2005/0177082 | A1 | 8/2005 | Bledsoe |
| 2005/0245853 | A1 | 11/2005 | Scorvo |
| 2005/0273025 | A1 | 12/2005 | Houser |
| 2006/0100560 | A1 | 5/2006 | Gilmour |
| 2006/0100561 | A1 | 5/2006 | Gilmour |
| 2006/0116616 | A1 | 6/2006 | Albrecht et al. |
| 2006/0135902 | A1 | 6/2006 | Ingimundarson et al. |
| 2006/0142680 | A1 | 6/2006 | Iarocci |
| 2007/0010772 | A1 | 1/2007 | Ryan |
| 2007/0050044 | A1 | 3/2007 | Haynes et al. |
| 2007/0100265 | A1 | 5/2007 | Gamada |
| 2007/0232972 | A1 | 10/2007 | Martinez |
| 2007/0270976 | A1 | 11/2007 | Deharde et al. |
| 2008/0051684 | A1 | 2/2008 | Gamada |
| 2008/0066272 | A1 | 3/2008 | Hammerslag et al. |
| 2008/0195013 | A1 | 8/2008 | Ingimundarson et al. |
| 2008/0200856 | A1 | 8/2008 | Cadichon |
| 2008/0249448 | A1 | 10/2008 | Stevenson et al. |
| 2008/0294079 | A1 | 11/2008 | Sterling et al. |
| 2009/0054819 | A1 | 2/2009 | Einarsson |
| 2009/0076426 | A1 | 3/2009 | Einarsson et al. |
| 2009/0099495 | A1 | 4/2009 | Campos et al. |
| 2009/0099562 | A1 | 4/2009 | Ingimundarson et al. |
| 2009/0105622 | A1 | 4/2009 | Sterling et al. |
| 2009/0124948 | A1 | 5/2009 | Ingimundarson et al. |
| 2009/0171469 | A1 | 7/2009 | Thorsteinsson et al. |
| 2009/0240181 | A1 | 9/2009 | Sreeramagiri et al. |
| 2009/0259154 | A1 | 10/2009 | Nace |
| 2009/0281637 | A1 | 11/2009 | Martin |
| 2009/0287128 | A1 | 11/2009 | Ingimundarson et al. |
| 2010/0010409 | A1 | 1/2010 | Bejarano |
| 2010/0056970 | A1 | 3/2010 | Nace |
| 2010/0162539 | A1 | 7/2010 | Rancon |
| 2011/0098618 | A1 | 4/2011 | Fleming |
| 2011/0270413 | A1 | 11/2011 | Haynes |
| 2012/0022667 | A1 | 1/2012 | Accinni et al. |
| 2012/0046585 | A1 | 2/2012 | Lee et al. |
| 2012/0059296 | A1 | 3/2012 | Kompa |
| 2012/0157902 | A1 | 6/2012 | Castillo et al. |
| 2013/0110020 | A1* | 5/2013 | Ingimundarson ..... A61F 5/0123 602/16 |
| 2013/0150761 | A1 | 6/2013 | Romo et al. |
| 2013/0172797 | A1* | 7/2013 | Merkley ............... A61F 5/0123 602/16 |
| 2013/0178771 | A1 | 7/2013 | Moir et al. |
| 2013/0331754 | A1 | 12/2013 | Dunn et al. |
| 2014/0213948 | A1 | 7/2014 | Romo et al. |
| 2015/0005685 | A1 | 1/2015 | Chetlapalli et al. |
| 2016/0151189 | A1 | 6/2016 | Romo et al. |

FOREIGN PATENT DOCUMENTS

| | | |
|---|---|---|
| DE | 196 45 076 A1 | 5/1998 |
| DE | 198 11 925 A1 | 10/1999 |
| DE | 10 259 751 A1 | 7/2004 |
| DE | 10 2010 006 089 A1 | 8/2010 |
| EP | 0 841 044 A1 | 5/1998 |
| EP | 0 941 722 A1 | 9/1999 |
| EP | 1 114 619 A1 | 7/2001 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2 828 093 A1 | 2/2003 |
| GB | 1 213 855 A | 11/1970 |
| WO | 86/04228 A1 | 7/1986 |
| WO | 9522700 A1 | 8/1995 |
| WO | 95/27451 A1 | 10/1995 |
| WO | 96/16615 A1 | 6/1996 |
| WO | 2004/056293 A1 | 7/2004 |
| WO | 2006/044423 A2 | 4/2006 |
| WO | 2009126724 A2 | 10/2009 |
| WO | 2010/087899 A2 | 8/2010 |

OTHER PUBLICATIONS

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf downloaded, 1 page.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", The American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom & OTS Knee Brace, "Application Instructions & Patient Manual: Instructions for ACL or PCL Symptoms", Jan. 2007, pp. 1-4, vol. CP020223, Rev B, Publisher: Bledsoe Brace Systems, Published in: US. http://www.bledsoebrace.com/pdf/Al/Axiom-Al.pdf.

Brochure: Armor Fourcepoint, Donjoy Product pages http://www.donjoy.com/armorfp. Downloaded, Oct. 2011, 2 pages. Published: US.

Brochure: "Fusion OA", Breg 360 Customer Care, Product page http://www.breg.com/knee-bracing/oa/fusion-oa.html, downloaded, Oct. 2011, 2 pages. Publisher: Orthofix, Published in: US.

Brochure: "Fusion XT OA", Bregg 360 Customer Care, Product page http://www.breg.com/knee-bracing/oa/fusion-xt-oa.html, downloaded, Oct. 2011, 2 pages. Publisher: Orthofix, Published in: US.

Brochure: "CTI Custom", Ossur Product page from http://www.ossur.com/?PageID=13230 downloaded, Oct. 2011, 2 pages. Publisher: Ossur Americas, Published in: US.

Brochure: "X2K-OA", Bregg 360 Customer Care, Product page http://www.breg.com/knee-bracing/oa/x2k-oa.html. Downloaded, Oct. 2011, 1 page. Publisher: Orthofix, Published in: US.

International Search Report and Written Opinion regarding Application No. PCT/US2011/051627, dated Jan. 6, 2012.

International Search Report from corresponding PCT Application No. PCT/US2012/062702, dated Feb. 15, 2013.

International Preliminary Report on Patentability regarding Application No. PCT/US2011/051627, dated Mar. 28, 2013.

Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservativ%20treatment.pdf, 37 pages.

Extended European Search Report from EP Application No. 12150517.6, dated May 22, 2012.

(56) References Cited

OTHER PUBLICATIONS

Smith, Sean D. et al., "Functional bracing of ACL injuries: current state and future directions", Knee Surgery Sports Traumatology Arthhroscopy, Springer, Apr. 27, 2013, 11 pages.

Knapik, Joseph J. et al., "Isometric, Isotonic and Isokinetic Torque Variations in Four Muscle Groups Through a Range of Joint Motion," Physical Therapy: Journal of the American Physical Therapy Association and de Fysiotherapeut, 1983, vol. 63, No. 6, pp. 938-947, downloaded from http://ptjournal.apta.org/ on Apr. 15, 2014.

International Search Report and Written Opinion from International Application No. PCT/US2014/013245, dated May 6, 2014.

Jansson, Kyle S. et al., "A Historical Perspective of PCL Bracing", Knee Surgery Sports Traumatology Arthhroscopy, Springer-Verlag, May 24, 2012, 7 pages.

International Search Report from corresponding International Application No. PCT/US2014/042989, dated Oct. 15, 2014.

* cited by examiner

ORTHOPEDIC DEVICE HAVING A DYNAMIC CONTROL SYSTEM

FIELD OF THE DISCLOSURE

This disclosure relates to an orthopedic device having a dynamic control system for providing variable assistance during gait, particularly as a user flexes a knee, and providing increased loading at certain flexion angles and diminished loading at other flexion angles and extension to provide stabilization at peak loading moments.

BACKGROUND

Conventional orthopedic braces embody a wide range of structures and serve the similar purpose of supporting and stabilizing a joint when worn on the body of a user. When used in this manner, such braces may help an existing injury heal, or prevent future injuries from occurring. A brace can add support and stability to a healthy skeletal joint to reduce the risk of injury when the joint is subjected to undue stress. Alternatively, braces may help provide relief and restore functionality to an injured person by providing stabilizing support to a weakened skeletal joint to reinforce it and reduce the risk of sustaining further injury. An orthopedic brace must be sufficiently secured to a user so it can provide the support and stability as needed.

Patients commonly wear orthopedic knee braces after surgery for treatment of an injury to the knee joint. Knee braces may serve many purposes. For instance, they stabilize the knee joint and control its lateral movement, or knee braces help limit joint flexion and/or extension in an adjustable and controllable manner to prevent recurrence of injury to the knee.

Certain types of knee injuries require special attention. An injury of the posterior cruciate ligament (PCL) would benefit from a PCL knee brace designed to provide support to the back of the upper calf throughout the range of motion to prevent unwanted shifting. In a recently injured or postoperative patient, this may also lessen the lengthening of the PCL during healing. For a patient with a PCL having healed in a lengthened state, the brace may prevent such undesirable shifting to give the patient the feeling of added stability. The tension in the PCL changes dynamically relative to the knee flexion angle. Therefore, the PCL brace may theoretically apply a correspondingly dynamic load to offset the tension in the posterior cruciate ligament.

Conventional PCL braces offer a strap that provides static ACL (anterior cruciate ligament) or PCL support, and the strap is often incorporated into a brace providing multiple ligaments stabilization. No known solutions have been provided which offer a dynamic load specifically for both the PCL and ACL, and an objective of the disclosure is to provide a dynamic controlling system for an orthopedic device.

One type of an ACL brace is found in U.S. Pat. No. 7,811,242 and features a hinge arranged to dampen a knee as it goes into extension. A posterior force is applied to the tibia, preventing anterior movement, which stresses the ACL, and reduces the anterior translation. The hinge is arranged to increase knee flexion angles to dampen knee extension and reduce shear forces at the knee.

An example of a device arranged to treat a weakened ACL is found in US patent application publication no. 2014/0213948, published Jul. 31, 2014, and incorporated by reference. The device of the '948 publication is limited in only treating the ACL and related issues. An example of a device arranged to treat a weakened PCL is found in US patent application publication no. 2013/0110020, published May 2, 2013, and incorporated by reference. An example of various systems for dynamically tensioning and preventing overtensioning forces or a mechanism to create compressive load on a wearer's anatomy and associated features therewith in an ACL or PCL brace is found in US patent application publication no. 2015/0005685, filed Jan. 1, 2015, having Ser. No. 14/311,548, filed on Jun. 23, 2014, and incorporated by reference.

SUMMARY

According to various embodiments, the orthopedic device includes dynamic control systems for individually treating both the ACL and the PCL as a function of flexion angle of a hinge system articulating according to a knee of a user. The orthopedic device is arranged for stabilizing the knee at peak loading moments for both the ACL and PCL, which are acknowledged as having different peak loading moments. From this arrangement, the orthopedic device provides different stabilization for different ligaments, as a knee undergoes movement between flexion and extension. The stabilization is dynamic because it varies according to the flexion angle of the orthopedic device in correspondence to rotation or angulation of the hinge system of the orthopedic device, and dual because stabilization occurs for both the ACL and PCL simultaneously but differently for each ligament.

An exemplary dynamic control system preferably has a first dynamic component on a first side of the orthopedic device, such as being positioned on the posterior thigh of a user to exert a first dynamic force on a user's thigh and femur in a first direction to accommodate an ACL, at a peak loading moment. A second dynamic component may also be on first side of the orthopedic device, such as being positioned on the posterior calf of a user to exert a second dynamic force on a user's calf and tibia in a second direction. The first and second dynamic components may be arranged separately from one another such that each may load the user's leg and knee at different flexion angles or vary in the load relative to one another that applies to the user's leg.

The orthopedic device may include a counterforce system adapted to counteract the first and second forces, with a first strap device along a user's upper leg counteracting the second force, and a second strap along a user's lower leg counteracting the first force. The counterforce strap device counteracts the first and second dynamic components according to articulation of the hinge or hinges to dynamically load the user's upper and lower legs according to individual loads applied by the first and second dynamic components.

While both the first and second dynamic components are in a single orthopedic device, they may operate independently of one another between extension and flexion. Natural forces on an ACL during flexion vary with the flexion angle and activity. The first dynamic component is adapted to replicate the force flexion behavior of the ACL, whereas the second dynamic component is adapted to apply correct anatomic joint forces that vary with the knee flexion angle. Both the first and second dynamic components are adapted to provide adjustability to satisfy the demands of various activities.

In an embodiment of the orthopedic device having a dynamic control system, the orthopedic device includes a frame with first and second struts connected to one another by a hinge system preferably including a hinge on both the medial and lateral sides of the orthopedic device. The dynamic control system may include a first dynamic component adapted for the ACL. The first dynamic component has a first cable and a first adjustment mechanism connected to the first cable and arranged to incrementally wind or release the first cable in the first direction relative to the first strut. The dynamic control system may include a second dynamic component adapted for the PCL. The second dynamic component includes a second cable and a second adjustment mechanism connected to the second cable and arranged to incrementally wind or release the second cable in the second direction relative to the second strut. The first direction is preferably generally the same as the second direction when the orthopedic device is in extension but will vary in flexion depending on the articulation of the hinge system. Each of the first and second adjustment mechanisms includes a loading element such as a shell applying a force against a user's leg in the first and second directions.

The dynamic control system may comprise a first guide on the first strut directing the first cable from the first adjustment mechanism past and over the hinge to a second guide on the second strut. The first cable may slidably extend through the first guide and terminate at the second guide such that a first end of the first cable is secured to the first adjustment mechanism and a second end of the first cable is secured to the second guide. The first cable may freely extend over the hinge.

The second cable may slidably extend through the second guide such that a first end of the second cable is secured to the second adjustment mechanism and a second end of the second cable is secured to the hinge. The second cable may extend obliquely from the second guide relative to the first cable extending to the second guide from the first guide. The first cable may generally extend over a center of the hinge when the orthopedic device is in extension and the second cable extends into the hinge at a corner inlet.

The second guide may include a first arcuate channel including an inlet through which the first cable extends and a termination point within the second guide at which a second end of the first cable terminates. A second channel may define an arcuate shape and has first and second outlets through which the second cable slidably extends. The second guide preferably defines a tapered recess at an inlet into which the first cable extends to accommodate a movement profile of the first cable as the hinge articulates. The second outlet can be formed proximate and outside the movement profile and the tapered recess may define a V-shaped profile.

The orthopedic device includes a counterforce system located on a second side of the orthopedic device relative to an anterior-posterior plane and adapted to counteract the first and second dynamic forces of the dynamic control system. The counterforce system preferably includes a first counterforce strap device coupled to the second strut and inferior to the hinge system for providing a first counteracting force to the first dynamic force. A second counterforce strap device is coupled to the first strut and superior to the hinge system for providing a second counteracting force to the second dynamic force.

In an embodiment of the counterforce system, a first counterforce strap device is coupled to the first strut and arranged to be dynamic by adjusting in tension on a user according articulation of the hinge. It may be that if straps counteracting the forces exerted by the first and second dynamic components are fully tightened, they may resist or negate the force provided by the first and second dynamic components. The counterforce strap device may be arranged to dynamically adjust according to articulation of the hinge.

The first counterforce strap device may include a first strap on a side of the first strut opposite the first adjustment mechanism and a third cable connecting the strap to the hinge. The first counterforce strap device includes a third guide secured to the first strut such that the third guide directs the third cable from the first strap to the hinge. A first end of the third cable secures to a first bracket upon which a first segment of the first strap is adjustably attached, and a second end of the third cable is secured to the hinge.

The counterforce system may include a second counterforce strap device coupled to the second strut and arranged to adjust in tension on a user according to articulation of the hinge. The second counterforce strap device may include features similar to the first counterforce strap device or may be a conventional static strap.

Various other straps and frame elements may be employed in combination with the orthopedic device, and the orthopedic device may include any of the features of the dynamic control system described herein. Dynamic components are provided to apply dynamic loads on the ACL and PCL according to flexion angle of a knee, whereas the counterforces can apply either static or dynamic counterforce in response to the dynamic loads of the dynamic components. The dynamic components may be arranged on either anterior or posterior sides of the knee.

A method for using the orthopedic device includes arranging a first dynamic component on a first side of the orthopedic device relative to an anterior-posterior plane, and superior to the hinge system. The first dynamic component connects to at least one of the first and second struts and exerts a first dynamic force directed toward at least one of the first and second struts of the orthopedic device according to a flexion angle of the hinge system. The method also involves arranging a second dynamic component on a first side of the orthopedic device relative to an anterior-posterior plane, and inferior to the hinge system. The second dynamic component connects to at least one of the first and second struts and exerts a second dynamic force directed toward at least one of the first and second struts according to a flexion angle of the hinge system.

The method further includes the step of application of a counterforce system to a second side of the orthopedic device relative to an anterior-posterior plane and counteracting the first and second dynamic forces. The counterforce system comprises a first counterforce strap device coupled to the second strut and inferior to the hinge system for providing a first counteracting force to the first dynamic force, and a second counterforce strap device coupled to the first strut and superior to the hinge system for providing a second counteracting force to the second dynamic force.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device, and in no way limit the structures or configurations of a liner according to the present disclosure.

DETAILED DESCRIPTION OF VARIOUS EMBODIMENTS

A. Overview

Figure 1:
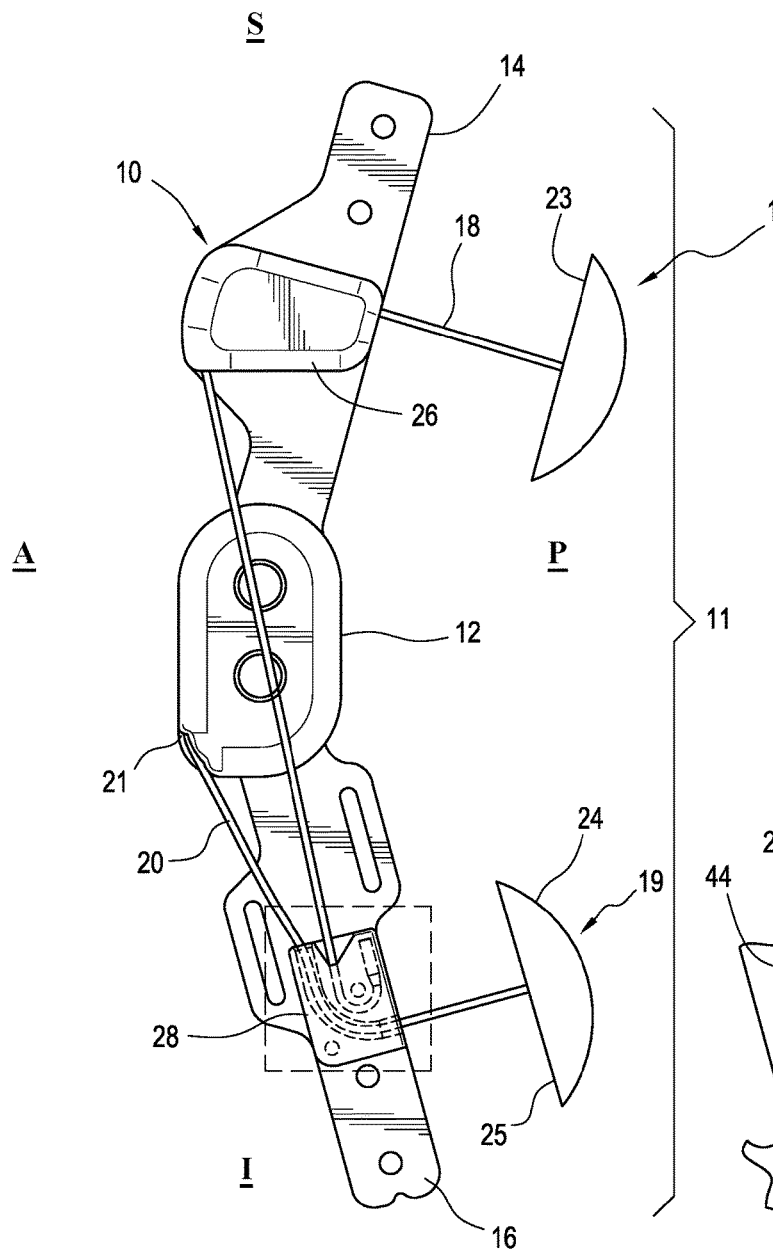
FIG. 1 is a side elevational schematic view of a dynamic control system located on first and second struts and a hinge of an orthopedic device.
Figure 2:
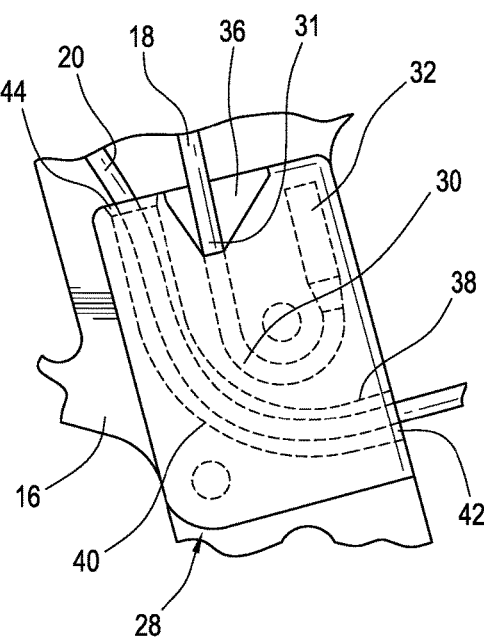
FIG. 2 is a detail of a second guide in the dynamic control system of FIG. 1.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the invention covers all modifications, alternative constructions, combinations, and equivalents falling within the spirit and scope of the disclosure.

It will be understood that, unless a term is expressly defined herein to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112, paragraph 6.

B. Definitions

For ease of understanding the disclosed embodiments of an orthopedic device, the anterior and posterior portions of the orthopedic device may be described independently. Anterior and posterior portions of the orthopedic device function together to support and stabilize anatomical portions of the user of the device.

For further ease of understanding the embodiments of an orthopedic device as disclosed, a description of a few terms, when used, is necessary. The term "posterior" also has its ordinary meaning and refers to a location behind or to the rear of another location. The posterior side is denoted in the figures as "P". The term "anterior" has its ordinary meaning and refers to a location ahead of or to the front of another location, such that the anterior and posterior sides are divided by an anterior-posterior plane. The anterior side is denoted in the figures as "A". The terms "proximal" and "distal" generally refer to locations of the device that correspond to the location of leg relative to the point of attachment of the leg to the body. The location where the device corresponds to the knee joint is used herein to generally delimit the proximal and distal sections of the device. "Superior" or above the hinge denotes location of components relative to the hinge, just as "inferior" or below the hinge. Superior of the hinge is denoted as "S" in the figures, and inferior of the hinge is denoted as "I" in the figures.

The terms "medial" and "lateral" are relative terms that are generally understood as indicating location regarding the midsaggital plane or midline. Therefore, elements located near the midline are "medial" and those elements further from the midline are "lateral." The term "central" is used to denote the area along the midline of a joint dividing and sharing regions of the medial and lateral regions.

The term "dynamic" has its ordinary meaning as a force occurring due to the motion of a mechanism, whereas the term "static" has its ordinary meaning as a force always present.

Flexion and extension are examples of angular motions, in which two axes of a joint are brought closer together or moved further apart. Extension is when the angle between the thigh bone or femur and the shin bone or tibia is generally 0 degrees. Flexion occurs as the knee bends from 0 degrees flexion to full flexion at about 135-145 degrees, depending on the muscle/fat bulk of the limb.

C. Various Embodiments of the Orthopedic Device

Referring to FIG. 1, the orthopedic device 10 includes a dynamic control system 11 for individually treating both the ACL and the PCL as a function of flexion angle of a hinge or hinges articulating according to a knee of a user. Examples of the ACL dynamic control system are found in US patent application publication no. 2014/0213948 and examples of the PCL dynamic control system are found in US patent application publication no. 2013/0110020. Various systems for dynamically tensioning and preventing overtensioning forces or a mechanism to create compressive load on a wearer's anatomy and associated features therewith in an ACL or PCL brace is found in U.S. patent application Ser. No. 14/311,548. Reference should be made to the aforementioned publications and application for details on the components described below.

FIG. 1 shows an orthopedic device 10 including the dynamic control system 11 including a first dynamic component 17 on a first side of the orthopedic device and may be positioned on the posterior thigh of a user to exert a first force on a user's thigh in a first direction to accommodate an ACL. The dynamic control system 11 also includes a second dynamic component 19 on a second side of the orthopedic device and may be positioned on the posterior calf of a user to exert a second force on a user's calf in the first direction. The first and second dynamic components 17, 19 may be arranged separately from one another such that each may load the user's leg and knee at different flexion angles or vary in the load relative to one another that is applied to the user's leg.

For simplicity, the dynamic control system 11 is shown on only one side of the orthopedic device, and both medial and lateral sides generally have the same arrangement of the dynamic control system 11 such that dynamic control system 11 uniformly operates on both medial and lateral sides of the orthopedic device. The orthopedic device likewise includes medial and lateral struts on a device similarly shown in both US patent application publication no. 2013/0110020 and US patent application publication no. 2014/0213948. The forces exerted by the first and second dynamic components 17, 19 generally operate symmetrically over the orthopedic device, along both the medial and lateral sides of the orthopedic device, but individually vary according to the flexion angle of hinges of the orthopedic device and location (e.g., proximally or distally).

Figure 5:
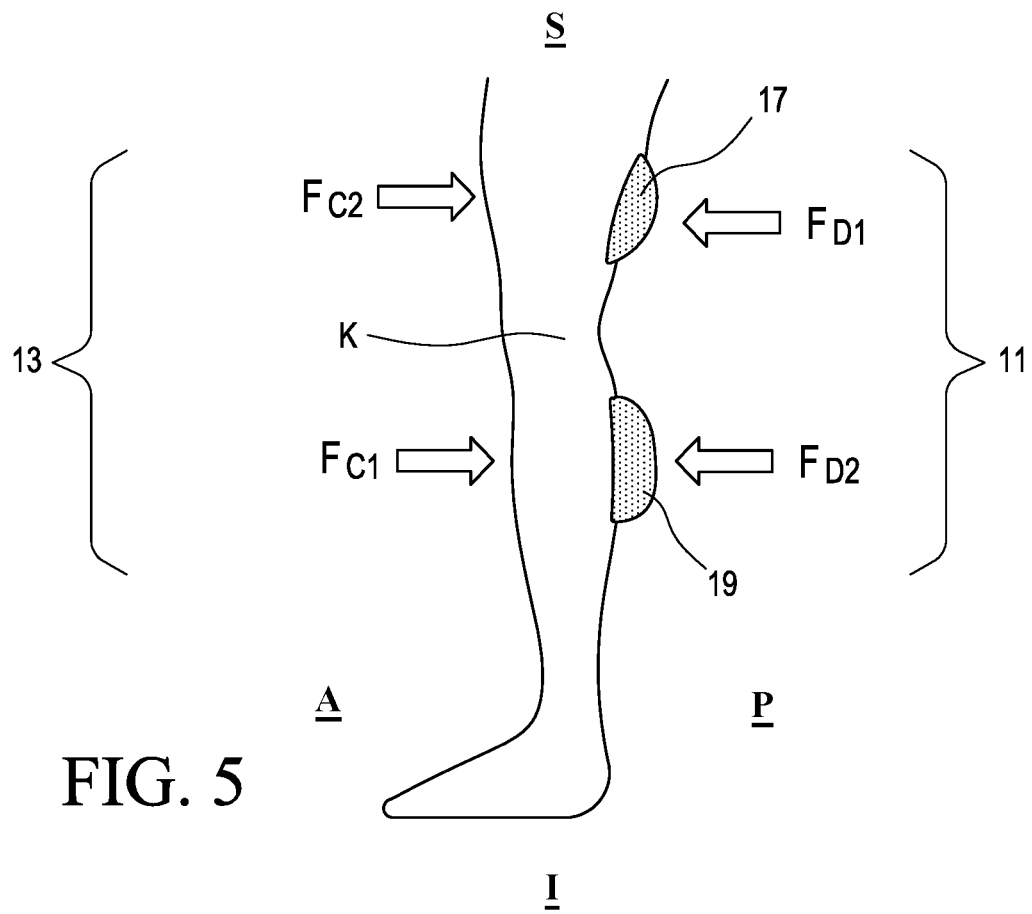
FIG. 5 is a force diagram of the forces from the counterforce strap device and the ACL and PCL dynamic components of FIG. 1.

For a better understanding of the actual forces applied by the dynamic control system 11 and a counterforce system 13, FIG. 5 shows how the dynamic components 17, 19 individually exert dynamic forces proximally and distally relative to the knee on the posterior side P of the orthopedic device, relative to static forces maintained by straps or frame elements counteracting the dynamic forces on the anterior side A of the orthopedic device. According to the embodiment of FIG. 1, FIG. 5 shows a first dynamic force FD1 applied to the posterior upper leg (back of the thigh) relative to the knee K, applied for stabilizing the ACL, and a first counterforce FC1 applied to the anterior lower leg (shin) relative to the knee K. Conversely, a second dynamic force FD2 is applied to posterior lower leg (calf) relative to the knee K, stabilizing the PCL, and a second counterforce FC2 applied to the anterior upper leg (front of the thigh) relative to the knee. While the counterforces FC1, FC2 may be static or dynamic, they are arranged to counteract the first and second dynamic forces FD1, FD2.

Figure 6:
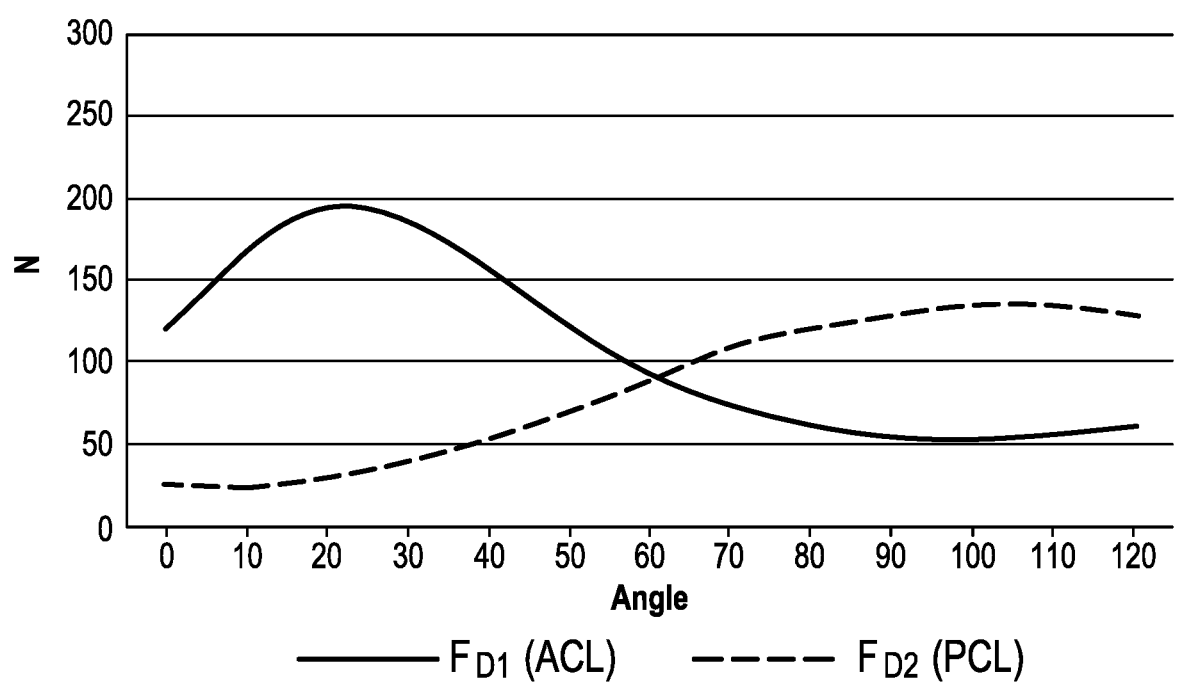
FIG. 6 is a graph showing average In Situ ACL and PCL load forces.

As depicted in FIG. 6, the loads exerted by the dynamic forces vary relative to articulation of the knee and are independent from one another. The first dynamic force or load provides kinematic constraint to a deficient ACL as a knee undergoes flexion by providing control to anterior tibial translation. As evidenced, the first dynamic force should ramp quickly from 0 degrees flexion to a maximum load at about 20 degrees flexion, after which a drop in force continues to and past 90 degrees flexion. Alternatively, the second dynamic force or load is intended to gradually increase, albeit not necessarily to the same maximum load as in the first dynamic force, to flexion of 90 degrees. The second dynamic force for the PCL aims to provide a posterior force onto the tibia and urge an anterior shift by providing resistance to posterior translation of the tibia relative to the femur.

Figure 7:
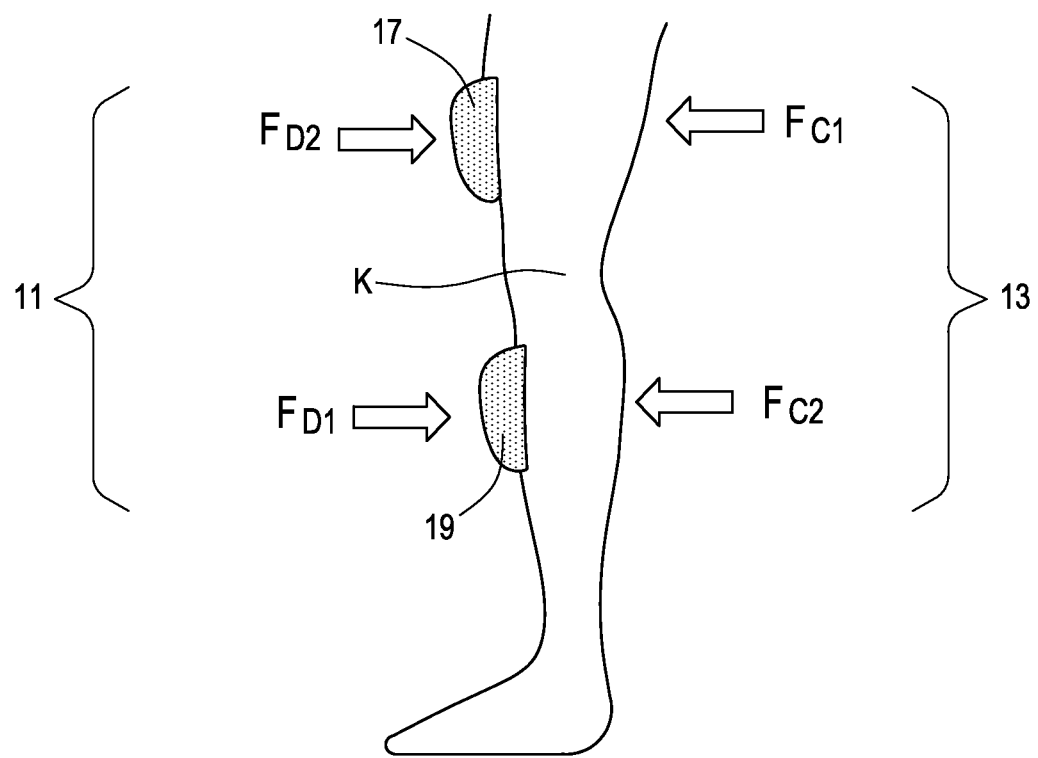
FIG. 7 is another force diagram of the forces from the counterforce strap device and the ACL and PCL dynamic components in a variation of FIG. 1.

FIG. 7 illustrates how the dynamic control system 11 and the counterforce system 13 are not limited to the configuration depicted in FIG. 5, and in correspondence to the embodiment of FIG. 1. Rather, the dynamic and counterforces can be rearranged while still performing the same function according to the illustration in FIG. 5. The critical consistency between the diagrams of FIGS. 5 and 7, is the application of dynamic forces on the knee that are counteracted on an opposed side, and preferably at a location on an opposite side of the leg and knee (relative to proximal/upper and distal/lower).

The counterforces may be static or dynamic according to flexion of the knee. With being a dynamic counterforce, various solutions known to one skilled in art are available such as connecting an element to a hinge of the orthopedic device and connecting the same to a strap, shell or other orthopedic device component. Alternatively, the strap may be elastically secured to the frame so that as the knee goes into flexion, the strap may loosen or tighten according to movement of the knee, as the leg alters in size and configuration according to extension and flexion.

According to an exemplary embodiment in FIGS. 1-4, the orthopedic device includes first and second struts 14, 16 connected to one another by a hinge system 12 preferably including hinges on both medial and lateral sides of the orthopedic device. The first dynamic component 17 includes a first cable 18 and a first adjustment mechanism 22 having a loading component 23 exerting force on the user's leg. The second dynamic component 19 includes a second cable 20 and a second adjustment mechanism 24 having a loading element 25 exerting force on the user's leg. Both the first and second dynamic components 17, 19 may be arranged with a loading component such as a shell and an adjustment device such as a dial tensioning mechanism, as taught in U.S. patent application Ser. No. 14/311,548.

The first dynamic component 17 is adapted for the ACL and is arranged to incrementally wind or release the first cable 18 in a first direction relative to the first strut 14. The second dynamic component 19 is adapted for the PCL and is arranged to incrementally wind or release the second cable 20 in a second direction relative to the second strut 16.

The dynamic control system 11 includes a first guide 26 on the first strut 14 directing the first cable from the first adjustment mechanism past and over the hinge 12 to a second guide 28 on the second strut 16. The first cable 18 may slidably extend through the first guide 26 and terminate at the second guide 28 such that a first end of the first cable 18 is secured to the first adjustment mechanism 22 and a second end of the first cable 18 is secured to the second guide 28. The first cable 18 may freely extend over a surface of the hinge system 12 such that the hinge 12 does not interfere with movement of the first cable 18 as the hinge 12 articulates.

The second cable 20 may slidably extend through the second guide 28 such that a first end of the second cable 20 is secured to the second adjustment mechanism 24 and a second end of the second cable 20 is secured to the hinge 12. The second cable 20 may extend obliquely from the second guide 28 relative to the first cable 18 extending to the second guide 28 from the first guide 26. The first cable 18 may generally extend over a center of the hinge 12 when the orthopedic device, including the struts 14, 16 and hinge 12, is in extension and the second cable 20 extends into the hinge at a corner inlet 21.

Interaction of the first cable 18 relative to the hinge is described in greater detail in US patent application publication no. 2014/0213948. The manner in which the second cable 20 functions and how it secures to the hinge 12 is described in greater detail in US patent application publication no. 2013/0110020. In a preferred embodiment, the first and second cables are not intended to interact with one another; rather they operate independently according to the dynamic loads described in connection with FIG. 5. The first and second cables are arranged apart and independently along each of their length from one another without interference between extension and flexion of the hinge.

While the first and second cables are independent from one another, both structurally and functionally, the second guide 28 may include a first arcuate channel 30 including an inlet 31 through which the first cable 18 extends and a termination point 32 within the second guide 28 at which a second end of the first cable 18 terminates. A second channel 40 may define an arcuate shape and has a corner inlet 42 and a corner outlet 44 through which the second cable 20 slidably extends. The second guide connects the first and second cables, although they may operate independently from another and the second guide maintains the first and second cables apart from one another. The second guide enables elimination of redundant or excessive parts, while assuring harmonization of the first and second dynamic components, and the dynamic control system as a whole.

The second guide 28 preferably defines a tapered recess 36 at the inlet 31 into which the first cable 18 extends to accommodate a movement profile of the first cable 18 as the hinge 12 articulates. The corner outlet 44 can be formed proximate and outside the movement profile so as not to interfere with movement of the first cable 18. The tapered recess 36 may define a V-shaped profile to accommodate movement of the first cable 18 between extension and flexion.

The location and structure of the second guide provides an exact or substantially exact termination point for the first cable for the first dynamic component 17 for ACL treatment activity, and the proper channel geometry to assure the second cable properly routes for proper PCL treatment activity.

Figure 3:
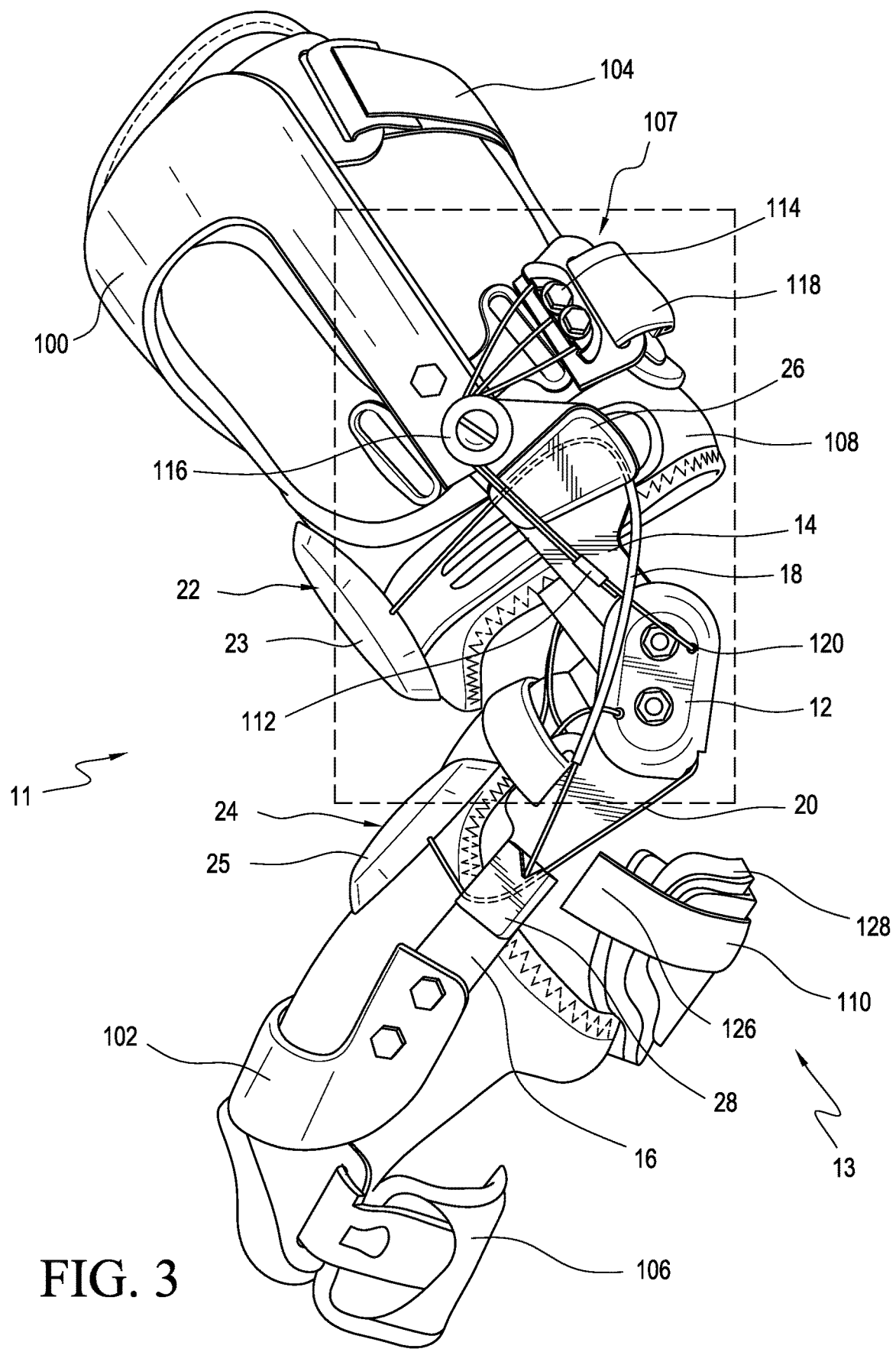
FIG. 3 is a schematic view of an orthopedic device including the dynamic control system of FIG. 1.

FIG. 3 shows an exemplary frame to the orthopedic device including first and second frame elements 100, 102 extending from and secured to the first and second struts 14, 16. Various straps 104, 106 may be provided to maintain the orthopedic device on the leg of a wearer, including a counterforce strap device. The counterforce strap device is adapted to counteract the first and second forces exerted by the first and second dynamic components 17, 19.

Figure 4:
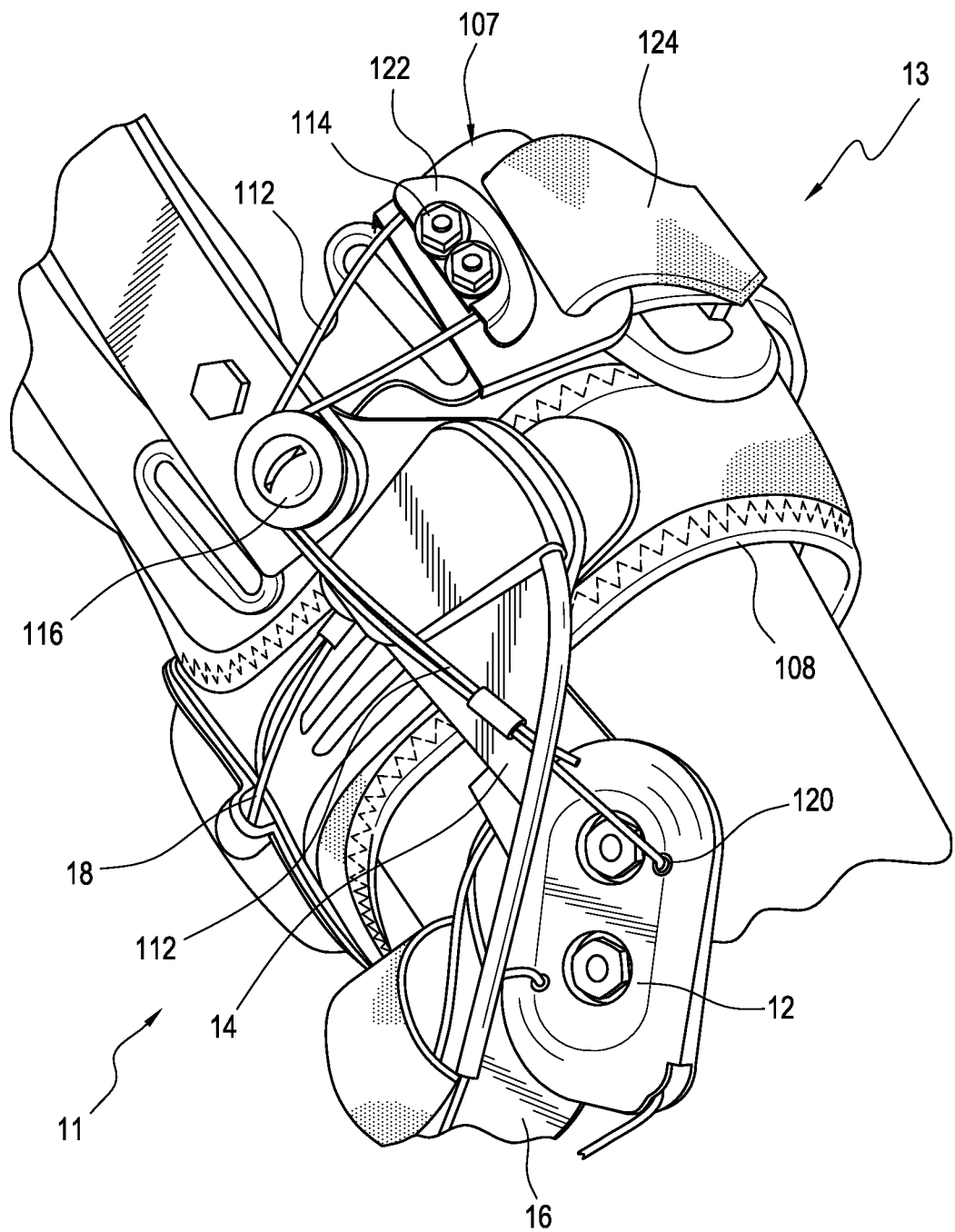
FIG. 4 is a detail view of a counterforce strap device in the orthopedic device of FIG. 3.

In the exemplary embodiment of FIGS. 3 and 4, a counterforce system 13 includes a first counterforce strap device 110 located below the hinge at a lower portion of the orthopedic device and is intended to extend along a user's anterior lower leg (shin) counteracting the first dynamic FD1 provided by the first dynamic component, 17, as also shown in FIG. 5. The first counterforce strap device 110 is static and is an example of providing a static counterforce FC1.

A second counterforce strap device 107 is above the hinge at an upper portion of the orthopedic device and is intended to extend along a user's anterior upper leg (thigh) counteracting the second dynamic force FD2 produced by the second dynamic component 19, as shown in FIG. 5. The second counterforce strap device 107 is dynamic and is an example of a providing a dynamic counterforce FC2.

The strap devices used for offering counterforces to the dynamic forces of the first and second dynamic components can be arranged as either static or dynamic strap devices. The first and second counterforce strap devices are provided by example, and are not limited to either one being static or dynamic, and may be reconfigured for being used interchangeably.

The first counterforce strap device 110 includes a strap 126 secured to opposed sides of the second strut 16, either directly or by a bracket such as a D-ring. While the strap 126 is adjustable in length, it does not dynamically change in length once the length is set, as in a conventional static strap, and secured to the leg of the user. The strap device 110 may have a shell 128 secured to the strap 126 for distributing forces on the leg, and may include padding as is known in the art of bracing.

The second counterforce strap device 107 counteracts the second dynamic component 19 according to articulation of the hinge or hinges to dynamically load the user's upper and lower legs according individual loads applied by the first and second dynamic components 17, 19. While serving as a counterforce to the second dynamic component 19, the second counterforce strap device 107 may dynamically offset both first and second dynamic components 17, 19, either alone or in combination with the first counterforce strap device, to perform functionality at prescribed angles of flexion of the hinge.

The second counterforce strap device 107 is connected to the first strut 14 and arranged to adjust in tension on a user according articulation of the hinge 12, thereby providing a dynamic counterforce rather than a static counterforce. The second counterforce strap device 107 includes the first strap 108 on an anterior side A of the first strut 14 opposite the first adjustment mechanism. A third cable 112 connects the first strap 108 to the hinge 12.

The second counterforce strap device 107 includes a third guide 116 secured to the first strut 14 such that the third guide 116 directs the third cable 112 from the first strap 108 to the hinge 12. The third guide 116 may be a pulley, boss or other deflecting type element capable of repeated sliding engagement with the third cable 112 as the hinge 12 articulates. A first end of the third cable 112 secures to a first bracket 122 upon which a first segment 124 of the first strap 108 is adjustably attached, and a second end of the third cable 112 is secured to the hinge 12 at inlet 120. The second end of the third cable 112 may be secured in any suitable manner to the hinge 12; including examples described in US patent application publication no. 2013/0110020 regarding the first cable 18.

Various other straps and frame elements may be employed in combination with the orthopedic device, and the orthopedic device may include any of the features of the dynamic control system described herein.

While the foregoing embodiments have been described and shown, alternatives and modifications of these embodiments, such as those suggested by others, may be made to fall within the scope of the invention. While the orthopedic device has been described in a knee brace, it will be understood that the principles described may be extended to other types of orthopedic devices.

The invention claimed is:

1. An orthopedic device having first and second struts connected to one another by a hinge system including at least one hinge, comprising:
   a dynamic control system including:
      a first dynamic component arranged on a first side of the orthopedic device relative to an anterior-posterior plane, and superior to the hinge system, the first dynamic component connected to at least one of the first and second struts and arranged to exert a first dynamic force directed toward at least one of the first and second struts according to a flexion angle of the hinge system, a first cable consisting of and terminating at first and second ends with the first end securing to the first dynamic component and extending along the first strut and past the at least one hinge inferiorly to the hinge system, the second end of the first cable anchored to the second strut; and
      a second dynamic component arranged on a first side of the orthopedic device relative to an anterior-posterior plane, and inferior to the hinge system, the second dynamic component connected to at least one of the first and second struts and arranged to exert a second dynamic force directed toward at least one of the first and second struts according to a flexion angle of the hinge system, a second cable consisting of and terminating at first and second ends with the first end securing to the second dynamic component and the second end anchoring to and terminating at the at least one hinge such that the second end does not extend superiorly past the at least one hinge and engages a corner inlet of the at least one hinge at the anterior and inferior side;
   a counterforce system located on a second side of the orthopedic device relative to an anterior-posterior plane and adapted to counteract the first and second dynamic forces with at least one counterforce;
   wherein the first and second cables are separate and independently adjustable relative to one another;
   wherein the first cable freely extends over the hinge system without interference with movement of the first cable as the hinge system articulates.

2. The orthopedic device of claim 1, wherein:
the first dynamic component includes a first adjustment mechanism arranged to incrementally wind or release the first cable about a spool in a first direction relative to the first strut;
the second dynamic component includes a second adjustment mechanism arranged to incrementally wind or release the second cable about a spool in a second direction relative to the second strut.

3. The orthopedic device of claim 2, further comprising a first guide on the first strut directing the first cable from the first adjustment mechanism past and over the hinge system to a second guide located on the second strut.

4. The orthopedic device of claim 3, wherein the second cable extends obliquely from the second guide relative to the first cable.

5. The orthopedic device of claim 4, wherein the first cable generally extends over a center of the hinge system when the orthopedic device is in extension and the second cable extends into the hinge system at a corner inlet.

6. The orthopedic device of claim 3, wherein the first cable slidably extends through the first guide and terminates at the second guide such that the first end of the first cable is secured to the first adjustment mechanism and the second end of the first cable is secured to the second guide.

7. The orthopedic device of claim 3, wherein the second guide includes a first arcuate channel including an inlet through which the first cable extends and a termination point within the second guide at which the second end of the first cable terminates, and a second channel defining an arcuate shape and having a corner inlet and a corner outlet through which the second cable slidably extends.

8. The orthopedic device of claim 2, wherein each of the first and second adjustment mechanisms include a shell arranged for applying the first and second dynamic forces in the first and second directions, respectively.

9. The orthopedic device of claim 2, wherein the first and second directions are in a same direction when the orthopedic device is in an extension configuration, and extend in a different direction when the orthopedic device is in a flexion configuration beyond extension.

10. The orthopedic device of claim 2, wherein the first and second adjustment mechanisms are located on a posterior side of the orthopedic device, such that the first adjustment mechanism is superior the hinge system, and that the second adjustment mechanism is inferior of the hinge system.

11. The orthopedic device of claim 2, further comprising a first guide on the first strut directing the first cable from the first adjustment mechanism past and over the hinge system to a second guide located on the second strut, the first cable slidably extending through the first guide and terminates at the second guide such that the first cable extends through a first channel of the second guide and the second end of the first cable is secured to the second guide at a terminal end of the first channel, the second cable slidably extending through the second guide in a different direction to the first cable through a second channel.

12. The orthopedic device of claim 1, wherein the counterforce system includes a counterforce strap device coupled to the first strut and arranged to dynamically adjust in tension according articulation of the hinge system.

13. The orthopedic device of claim 12, wherein the counterforce strap device includes a first strap located on a second side of the orthopedic device relative to an anterior-posterior plane, the counterforce strap device provides a dynamic counterforce to the second dynamic force.

14. The orthopedic device of claim 12, wherein the counterforce strap device further includes a third cable connecting the strap to the hinge system and a third guide secured to the first strut such that the third guide directs the third cable from the first strap to the hinge system.

15. An orthopedic device having first and second struts connected to one another by a hinge system including at least one hinge, comprising:
a dynamic control system including:
a first dynamic component arranged on a first side of the orthopedic device relative to an anterior-posterior plane, and superior to the hinge system, the first dynamic component connected to at least one of the first and second struts and arranged to exert a first dynamic force directed toward at least one of the first and second struts according to a flexion angle of the hinge system, a first cable consisting of first and second ends with the first end securing to the first dynamic component and extending along the first strut and past the at least one hinge inferiorly to the hinge system, the second end of the first cable anchored to the second strut; and
a second dynamic component arranged on a first side of the orthopedic device relative to an anterior-posterior plane, and inferior to the hinge system, the second dynamic component connected to at least one of the first and second struts and arranged to exert a second dynamic force directed toward at least one of the first and second struts according to a flexion angle of the hinge system, a second cable consisting of first and second ends with the first end securing to the second dynamic component and the second end anchoring to and terminating at the at least one hinge such that the second end does not extend superiorly past the at least one hinge;
a counterforce system located on a second side of the orthopedic device relative to an anterior-posterior plane and adapted to counteract the first and second dynamic forces with at least one counterforce;
a first guide on the first strut directing the first cable from a first adjustment mechanism past and over the hinge system to a second guide located on the second strut, the first cable slidably extending through the first guide and terminates at the second guide such that the first cable extends through a first channel of the second guide and the second end of the first cable is secured to the second guide at a terminal end of the first channel, the second cable slidably extending through the second guide in a different direction to the first cable through a second channel;
wherein the first and second cables are separate and independently adjustable relative to one another.

16. The orthopedic device of claim 15, wherein the first cable freely extends over the hinge system without interference with movement of the first cable as the hinge system articulates.

* * * * *